United States Patent [19]

DeVries

[11] Patent Number: 5,443,448
[45] Date of Patent: Aug. 22, 1995

[54] DUAL FLEXIBLE INTRODUCER AND CANNULA

[75] Inventor: James H. DeVries, Grand Rapids, Mich.

[73] Assignee: DLP, Inc., Grand Rapids, Mich.

[21] Appl. No.: 251,093

[22] Filed: May 31, 1994

Related U.S. Application Data

[60] Division of Ser. No. 27,506, Mar. 5, 1993, Pat. No. 5,344,399, which is a continuation-in-part of Ser. No. 888,517, May 26, 1992, abandoned.

[51] Int. Cl.⁶ .......................................... A61M 25/00
[52] U.S. Cl. .................................... 604/96; 604/164
[58] Field of Search .................. 604/96, 95, 98, 101, 604/164, 170; 606/191, 194; 128/657, 772

[56] References Cited

U.S. PATENT DOCUMENTS

| | | | |
|---|---|---|---|
| 4,044,765 | 8/1977 | Kline | 604/164 |
| 4,368,730 | 1/1983 | Sharrock | 604/164 |
| 4,554,929 | 11/1985 | Samson et al. | 128/772 |
| 4,639,252 | 1/1987 | Kelly et al. | 604/282 |
| 4,763,647 | 8/1988 | Gambole | 604/164 |
| 4,811,743 | 3/1989 | Stevens | 128/657 |
| 4,813,434 | 3/1989 | Buchbinder et al. | 128/657 |
| 4,846,186 | 7/1989 | Box et al. | 128/772 |
| 4,886,067 | 12/1989 | Palermo | 604/164 |
| 4,940,062 | 7/1990 | Hampton et al. | 128/772 |
| 4,964,409 | 10/1990 | Tremulis | 604/164 |
| 4,994,036 | 2/1991 | Biscoping et al. | 604/164 |
| 5,021,045 | 6/1991 | Buckberg et al. | 604/53 |
| 5,065,769 | 11/1991 | de Toledo | 128/657 |
| 5,147,317 | 9/1992 | Shank et al. | 128/657 |

Primary Examiner—John D. Yasko
Attorney, Agent, or Firm—Barnes, Kisselle, Raisch, Choate, Whittemore & Hulbert

[57] ABSTRACT

A removable stylet for use in the introduction of cannulae into a vessel or chamber of a body for medical procedures, and a retrograde coronary sinus perfusion cannula using such stylet. The stylet is used to guide the cannula during insertion, and includes a proximal relatively stiff end that can be manually manipulated by the attending physician to guide the stylet. On the distal end of the stylet is a relatively flexible portion that can be shaped into various curves and which is form-retaining while retaining flexibility.

7 Claims, 2 Drawing Sheets

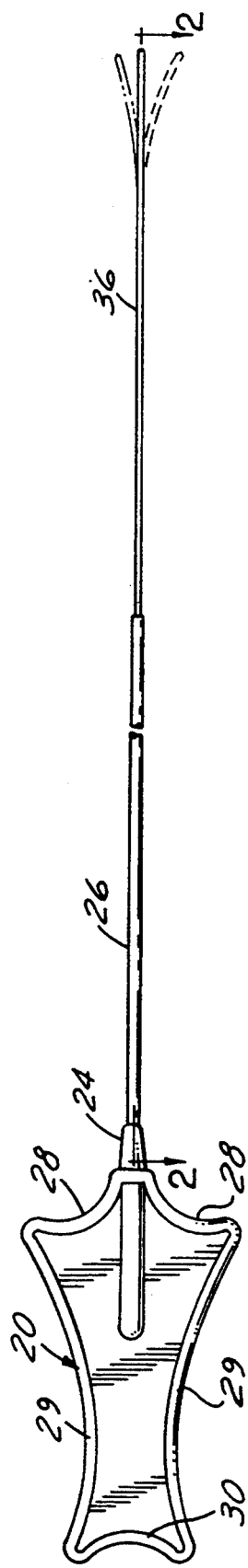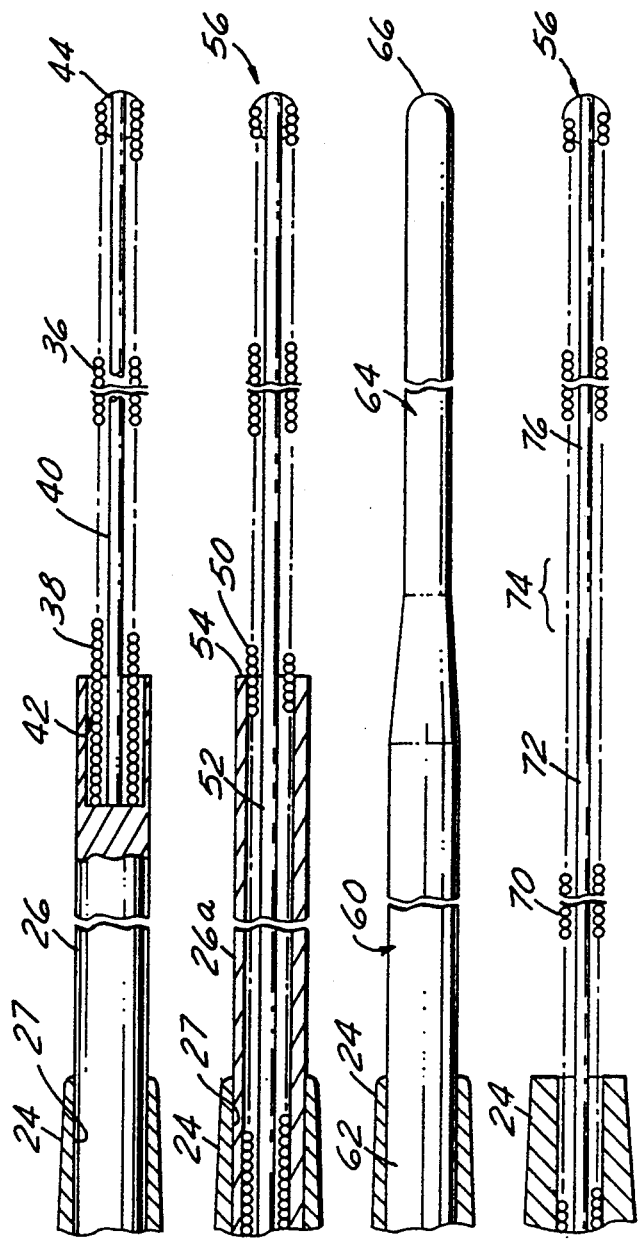

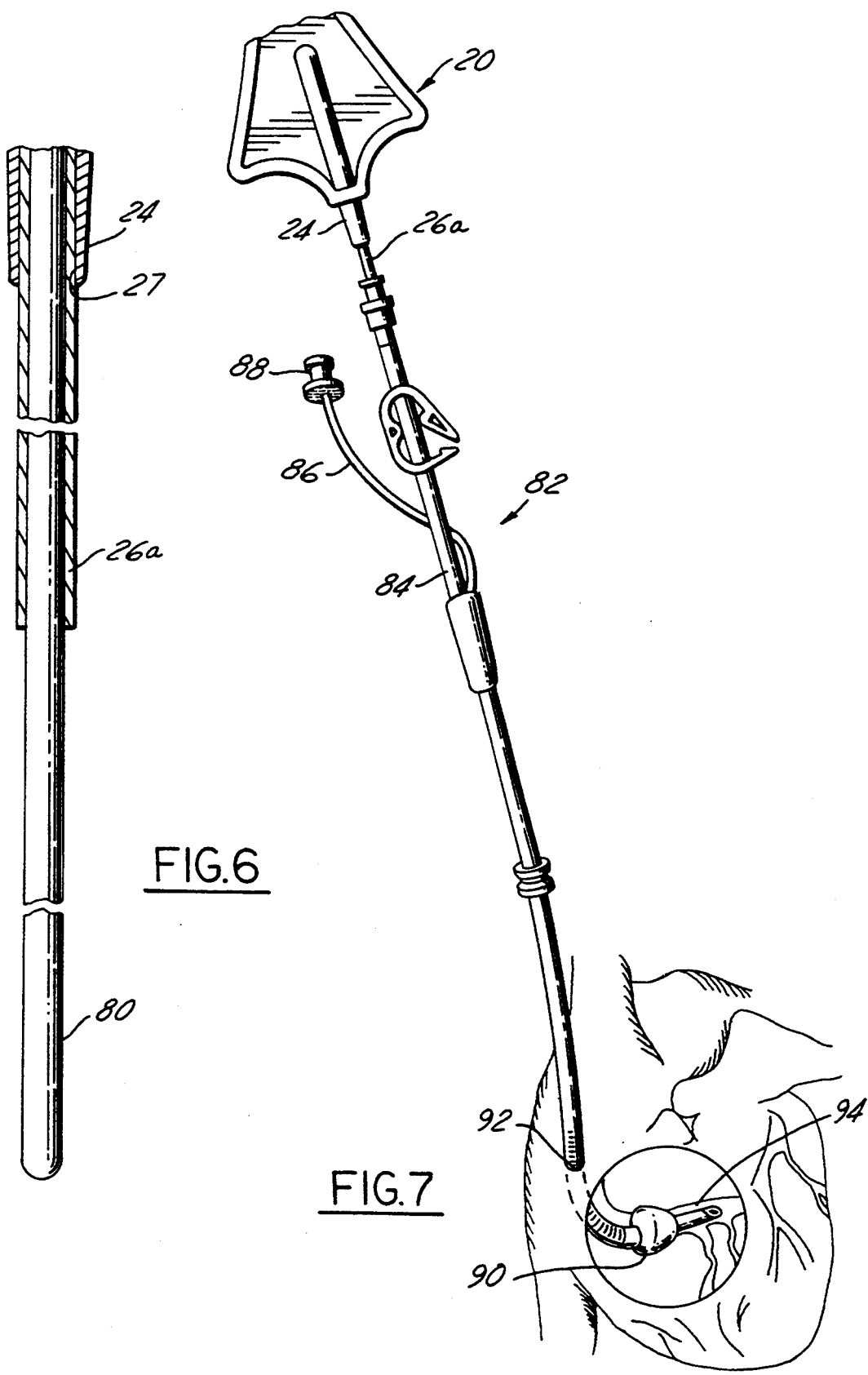

DUAL FLEXIBLE INTRODUCER AND CANNULA

This application is a division of Ser. No. 08/027,506, filed Mar. 5, 1993, which is now U.S. Pat. No. 5,344,399, which is a continuation-in-part of application Ser. No. 07/888,517, filed May 26, 1992 now abandoned.

Cannulae used with introducer stylets for retrograde coronary sinus perfusion and other flexible cannulae using introducer stylets.

BACKGROUND AND FEATURES OF THE INVENTION

Cannulae with introducer stylets are used for introduction into various organs of the body to introduce or withdraw fluids. One such use is a retrograde coronary sinus perfusion cannulae used in connection with open heart surgery. The cannula itself may be flexible, but the stylet within the cannula has sufficient rigidity that the combined cannula and stylet may be manipulated by a handle on the cannula to project into the selected organ of the body. Usually the stylet is withdrawn from the cannula after the successful introduction.

It is often desirable to place these types of flexible cannulae in friable vessels of the body having tortuous paths. A stylet having essentially uniform characteristics over the entire length of the cannula has typically been used. This conflicts with the necessity for the person placing the device to have a relatively stiff guiding stylet to locate the tip of the catheter near the desired opening or ostium, yet also embody flexibility to be self-guiding and atraumatic within vessels. By having two distinctly different types of construction or material characteristics along the stylet, each section can be appropriately tailored to meet these two criteria.

Retrograde coronary sinus perfusion cannulae in particular would benefit from an introducer stylet having a stiff proximal end and a flexible shape-retaining distal end. This type of cannula must be introduced through a small hole formed in the right atrium, and then moved through the interior of the atrium into coronary sinus ostium. The latter movement must be essentially blind, with the surgeon having to function by feel through the back heart wall. It would therefore be highly desirable to be supplied with an introducer stylet that may be bent at the distal end into a curve that suits the size of the heart, and yet possess a relatively stiff distal end that may be manipulated to advantage by the surgeon.

The present invention is directed to an improved removable cannula introducer in which there is a variable stiffness embodied in the length of the introducer, from a relatively stiff proximal portion to a more flexible yet shape-retaining distal end. While the overall length of the cannula and stylet may vary for different applications, an appropriate example is a 12" length not including the manipulative handle that is attached to the stylet. The invention is also directed to a retrograde coronary sinus perfusion cannula that employs such an introducer. The cannula comprises an elongated flexible tube with a central perfusion lumen and an integral side lumen for pressure monitoring. An inflatable cuff encircles the tube adjacent to the distal end thereof, and may be either self-inflating through communication with the central lumen or air-inflatable through a second side lumen. The introducer is assembled to the cannula by insertion from the proximal end into the central lumen.

An object of the invention is to provide a reinforcing introducer stylet for a cannula, the stylet having a handle to be used by the physician to manipulate the introduction. Another object of the present invention is to provide, for a relatively flexible cannula, a removable introducer stylet that provides proximal control stiffness and distal flexibility properly to install the cannula prior to removal of the introducer stylet.

Other objects and features of the invention will be apparent in the following description and claims in which the principles of the invention are set forth together with details to enable persons skilled in the art to apply the principles and techniques of the invention, all in connection with the best mode presently contemplated for the invention.

BRIEF DESCRIPTION OF THE DRAWINGS

DRAWINGS accompany the disclosure and the various views thereof may be briefly described as:

FIG. 1, a side elevation of a cannula stylet.

FIG. 2, a sectional view on line 2—2 of FIG. 1.

FIG. 3, a sectional view of a first modification of the stylet.

FIG. 4, a view of a second modification.

FIG. 5, a view of a third modification.

FIG. 6, a fragmentary section view of a fourth embodiment of the introducer stylet.

FIG. 7, a schematic diagram of a retrograde coronary sinus perfusion cannula with introducer stylet in accordance with the invention.

DETAILED DESCRIPTION OF THE INVENTION

With reference to the drawings in FIG. 1, a stylet manipulative handle 20 is illustrated. This handle has a distal end 24 in the form of a conical boss that receives and retains the proximal end of a tube 26 in a recess 27. From this boss 24 the handle extends to each side in a finger grip rib 28 and rearwardly in side extensions 29. A palm portion 30 connects the side extensions rearwardly of the handle.

The proximal portion 26 of the stylet in FIG. 1 is formed of a slender rod or tube which is relatively rigid. By this is meant that it cannot be readily bent with the fingers. The distal end of the stylet is formed of a portion 36 which is flexible in the sense that it is form- or shape-retaining but can be flexed easily. As shown in FIG. 2, this distal portion is formed of a tightly coiled spring 38 with a flexible core element 40 of malleable wire. The elements 38,40 may be joined to a recess 42 in the element 26 by an epoxy glue. The length ratio of rigid to relatively flexible may be 50/50 or possibly 2/3 rigid and 1/3 flexible. The diameter of portion 26 can be in the range of 1.5 millimeter and diameter of the flexible portion can be in the range of 1.25 millimeter as examples. The end of the core element 40 is joined to the distal end of the coil 38 in a smooth, rounded connection 44.

In FIG. 3, a modified stylet is illustrated. The slender tube 26a is mounted and retained in the recess 27 of handle boss 24. The tightly coiled spring portion 50 of the stylet extends within the tube 26a into the boss 24, and a flexible core element 52 of malleable wire within the coil also extends into the boss 24. As in the embodiment of FIG. 1, the coil 50 and the core element 52 are retained in the boss 24 by an epoxy material or other suitable retention means. In this embodiment, the coil 50 and the core element extend beyond the end 54 of the tube 26 to a distal end 56. This extension portion is the flexible shape-retaining component of the assembly, while the tube 26a is the relative rigid component.

In FIG. 4, a third embodiment is illustrated. This embodiment includes the boss 24, but the stylet is formed as a unitary element with a stiff proximal portion 60 having a proximal end 62 recessed and retained in the boss, while a reduced distal end 64 with a rounded tip 66 is integral with the proximal portion 60. In the heat treating of the portions 60 and 64, the reduced end is annealed to render it flexible as the distal end of the device. The characteristics of the rigid and flexible portions as outlined above pertain here also.

In the embodiment of FIG. 5, the boss 24 mounting the proximal end of a combination coil and core shaft assembly, namely, the tightly coiled spring coil 70 and the core shaft 72. In this embodiment the core shaft is formed as a rigid shaft down to an area 74, distally of which the shaft 76 is annealed to a soft and flexible core element.

The embodiment of FIG. 6 is similar to the embodiment of FIG. 3, except that the coil 50 and core 52 of FIG. 3 are replaced by a larger core 80 of malleable wire that fits closely within the inner diameter of tube 26a. In this embodiment, the malleable wire itself is of uniform cross section and stiffness throughout its length. In both of the embodiments of FIGS. 3 and 6, the central portions of the stylet, core 40 and coil 38 in FIG. 3 and core 80 in FIG. 6, are of uniform flexibility through their lengths, the proximal ends of the assemblies being stiffened by the surrounding tubes 26a. In both of these embodiments, both the central portions and the surrounding tube extend into and are imbedded in the handle. In two working examples of these embodiments, the overall length of the central portions are about 12 inches, and the length of tube 26a are about 4½ inches.

FIG. 7 illustrates a retrograde coronary sinus perfusion cannula 82 that includes the introducer of FIG. 3 or 6 as part of the assembly. An elongated flexible tube 84 has a central perfusion lumen into which the introducer is removably received. A pressure monitor side lumen is connected by a tube 86 to a lehr fitting 88. A cuff 90 surrounds the distal end of tube 84, and communicates with the central lumen for self-inflation by fluid flowing therethrough. With the exception of the introducer, cannula 82 is as shown in U.S. application Ser. No. 07/537,566, assigned to the assignee hereof and incorporated herein by reference for details of construction.

With the introducer of the present invention, cannula 82 may be preformed to have the curved distal end as shown, which is then inserted through the small hole 92 (precut and secured with a pursestring suture) into the right atrium. The stiff proximal end of the introducer, and thus the cannula 82 with introducer therein, greatly facilitates manipulation by the surgeon to feed the distal end essentially blind through the atrium into the coronary sinus ostium 94.

With these embodiments, the surgeon can readily control the insertion of a combined cannula and stylet by gripping the handle 20 and having good control of the relatively rigid proximal portions 26,26a, 60 and 70 of the various embodiments. The flexible end of the cannula can be formed by the surgeon into a desired shape for the particular insertion and will retain this shape while being flexible enough to adapt to various curves in the vessel being entered. This also permits guidance of the flexible distal ends into, for example, a coronary sinus and allows the distal end to move into the body organ without undesired perforation or blocking of the insertion thrust. Once the combined cannula stylet is introduced to the proper location, the stylet is removed by withdrawing the handle leaving the cannula in position.

What is claimed is:

1. A flexible cannula having an interior lumen and a distal end to be introduced into body vessels and chambers for medical procedures, and a removable introducer stylet to be carried in said lumen comprising a relatively rigid proximal end portion to be manipulated by an attendant physician and a relatively flexible distal end, said stylet comprising an integral shaft heat treated to render the distal end more flexible than the proximal end.

2. A cannula and stylet combination as defined in claim 1 in which said stylet comprises a metallic shaft, the distal end of which is annealed to a soft and flexible but shape retaining condition.

3. An introducer stylet for medical cannulation that comprises:
   a handle for manipulation by a user, and
   elongated guide means affixed to and extending from said handle, said guide means comprising a solid length of metallic composition that is heat treated such that the portion of said length adjacent to said handle is stiff and the portion remote from said handle is shape-retaining and more flexible than the portion adjacent to said handle.

4. The stylet set forth in claim 3 wherein said solid length is of non-uniform cross section, being of lesser diameter remote from said handle than adjacent to said handle.

5. The stylet set forth in claim 3 wherein said solid length is of uniform cross section throughout its length.

6. The stylet set forth in claim 5 wherein said guide means further comprises a tightly coiled spring surrounding at least that portion of said length remote from said handle.

7. The stylet set forth in claim 6 wherein said spring is affixed to and extends from said handle, surrounding the entire length of said solid length.

* * * * *